US006308703B1

(12) United States Patent
Alving et al.

(10) Patent No.: US 6,308,703 B1
(45) Date of Patent: *Oct. 30, 2001

(54) VENTILATOR DEVICE

(76) Inventors: Kjell Alving, Spetsvagen 40, 757 57 Uppsala; Jan M. Lundberg, Helgevagen 10, 182 64 Djursholm; Jon Lundberg, St. Eriksgatan 116, 113 31 Stockholm; Eddie Weitzberg, Nybrogatan 24, 114 39 Stockholm, all of (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/292,598

(22) Filed: Apr. 16, 1999

Related U.S. Application Data

(60) Division of application No. 08/786,789, filed on Jan. 21, 1997, now Pat. No. 6,019,100, which is a continuation-in-part of application No. PCT/SE96/00912, filed on Jul. 4, 1996.

(30) Foreign Application Priority Data

Jul. 5, 1995 (SE) .................................................. 9502442

(51) Int. Cl.[7] .................................................. A61M 15/00
(52) U.S. Cl. .................................. 128/203.12; 128/204.22
(58) Field of Search .................. 128/203.12, 204.22, 128/203.18, 205.13, 205.17, 205.19, 914

(56) References Cited

U.S. PATENT DOCUMENTS

| | | | |
|---|---|---|---|
| 3,766,914 | 10/1973 | Jacobs | 128/205.19 |
| 4,016,876 | 4/1977 | Martin et al. | 128/204.23 |
| 4,112,938 | * 9/1978 | Jeretin | 128/204.22 |
| 4,150,670 | 4/1979 | Jewett et al. | 128/204.22 |
| 4,631,966 | 12/1986 | Brugnoli | 128/204.22 |
| 4,702,241 | 10/1987 | Gravenstein et al. | 128/205.19 |
| 5,046,491 | 9/1991 | Derrick | 128/200.24 |
| 5,081,871 | 1/1992 | Glaser | 73/863.23 |

(List continued on next page.)

FOREIGN PATENT DOCUMENTS

| | | |
|---|---|---|
| 9347374 | 9/1992 | (AU) . |
| 640357A1 | 6/1994 | (EP) . |
| 9114469 | 10/1991 | (WO) . |
| 9119526 | 12/1991 | (WO) . |
| 9210228 | 6/1992 | (WO) . |
| 9305709 | 4/1993 | (WO) . |
| 9510173 | 10/1994 | (WO) . |
| 9502181 | 1/1995 | (WO) . |
| WO95/10173 | * 4/1995 | (WO) . |

OTHER PUBLICATIONS

Observanda—Swedish Medical Products Agency: Guidelines for the use of nitric oxide . . . (Apr. 25, 1995).
K. Alving et al., *Eur. Respir. J.*, vol. 6, pp. 1368–1370 (1993).
H. Gerlach et al., *The Lancet*, vol. 343, pp. 518–519 (Feb. 26, 1994).
E. Anggard, *The Lancet*, vol. 343, pp. 1199–1206 (May 14, 1994).
L. Puybasset et al., *Intensive Care Med.*, pp. 319–327 (1994).
J. Lundberg et al., *Eur. Respir. J.*, vol. 7, pp. 1501–1504 (1994).
Lundberg et al., *Nature Medicine*, vol. 1, No. 4, pp. 370–373 (Apr. 1995).
P. M. Dupuy et al., *J. Clin. Invest.*, vol. 90, pp. 421–428 (Aug. 1992).

*Primary Examiner*—Aaron J. Lewis
(74) *Attorney, Agent, or Firm*—Birch, Stewart, Kolasch & Birch, LLP

(57) ABSTRACT

The present invention restores the normal low-dose flushing of the lower airways with air from the upper airways, containing nitric oxide (NO) and possible other biologically active agents by aspiration of air from the upper airways and introducing said air in the inspiratory airflow of a ventilator. The inventive apparatus and method is free from the risks associated with traditional administration of exogenous NO.

9 Claims, 4 Drawing Sheets

U.S. PATENT DOCUMENTS

| | | | |
|---|---|---|---|
| 5,320,093 | * 6/1994 | Raemer | 128/203.12 |
| 5,373,841 | 12/1994 | Kyllonen et al. | 128/203.18 |
| 5,423,313 | * 6/1995 | Olsson et al. | 128/204.22 |
| 5,447,165 | * 9/1995 | Gustafsson | 600/532 |
| 5,651,358 | 7/1997 | Briend et al. | 128/204.22 |
| 5,699,790 | 12/1997 | Bathe et al. | 128/204.22 |
| 5,765,558 | 6/1998 | Psaros et al. | 128/207.14 |
| 5,795,787 | 8/1998 | Silkoff et al. | 128/201.18 |
| 6,019,100 | * 2/2000 | Alving et al. | 128/203.12 |

* cited by examiner

VENTILATOR DEVICE

CROSS-REFERENCE TO RELATED APPLICATIONS

This application is a 37 C.F.R. §1.53(b) divisional of U.S. application Ser. No. 08/786,789 filed on Jan. 21, 1997, now U.S. Pat. No. 6,019,100, which is a continuation-in-part of PCT International Application No. PCT/SE96/00912 filed on Jul. 4, 1996, which designates the United States. The entire contents of these applications are hereby incorporated by reference.

FIELD OF THE INVENTION

The present invention relates to the collection of naturally occurring gases from the upper airways in an intubated or tracheostomized mammal, said gases including biologically active agents, e.g. gaseous nitric oxide (NO) from endogenous sources; and the introduction of said gases, including said agents, e.g. NO in the inspiratory airflow from a ventilator.

DESCRIPTION OF THE BACKGROUND OF THE INVENTION

Healthy humans normally breathe mostly through the nose, whereby the upper airways and especially the nasal cavity serves to regulate the temperature and humidity of the inhaled air. But the upper airways do not only function as an ingenious heat exchanger and humidifier; they are also thought to be the source of endogenous, biologically active agents, such as endogenous nitric oxide (NO).

Nitric oxide (NO) is synthesized from the amino acid arginine by specific enzymes (NO-synthase) present in many cell types in the human body. Endogenous NO is thought to play a key role as an effector molecule with many biological effects including vasodilatation, neurotransmission and host defence. The biological effects of NO are mostly attributed to its rapid reaction with certain iron-containing enzymes resulting in either activation or inactivation of the enzyme. For example, NO produced in vascular endothelium diffuses to smooth muscle cells and binds to the heme moiety of soluble guanylate cyclase resulting in activation of the enzyme, formation of cyclic GMP and subsequently vasodilatation. NO produced by e.g. activated macrophages, may also have bacteriostatic and antiviral properties, thereby contributing to unspecific host defense.

Inhalation of exogenous NO gas has been used to reduce pulmonary vascular resistance in subjects with pulmonary hypertension. NO acts as a dilator of the pulmonary circulation when administered by the inhalation route. As soon as NO reaches the circulation it reacts with e.g. haemoglobin and is inactivated. Thus, NO may act selectively on pulmonary and bronchial circulation without affecting systemic circulation. Clinical trials are presently performed to explore the clinical outcome of exogenous NO inhalation in the treatment of certain pulmonary vascular disorders.

It is essential to handle exogenous NO with extreme caution, since high doses may be very dangerous, even lethal. NO reacts rapidly with oxygen to form $NO_2$. Higher doses of $NO_2$ may result in delayed haemorrhagic pulmonary edema. Furthermore, high concentrations of inhaled NO may result in methaemoglobinaemia due to competitive interaction with oxygen binding to haemoglobin.

Due to the above mentioned dangers of exogenous NO, it is vital to most carefully monitor the amounts of NO and $NO_2$ in inhaled air of patients receiving inhalation NO therapy. This may be carried out by connecting a $NO/NO_2$ analyzer (e.g. an apparatus using chemiluminescence technique) for on-line registration of $NO/NO_2$ concentrations in the inspirational airflow leaving the ventilator and distributed to the patient. Additionally, due to the rapid reaction of NO with oxygen, compressed NO gas must be kept in gas bottles free from oxygen. The gas administered to the patient should also be led through $NO_2$ scavenging arrangements, such as containers with soda lime.

The guidelines concerning therapeutic use of NO, issued by the Swedish Medical Products Agency (Läkemedelsverkets riktlinjer för användning av kvävemonoxid på licens i samband med ventilator be handling, Apr. 25, 1995) emphasize the risks associated with formation of $NO_2$. Acute toxic effects are known and possible mutagenic effects can not be ruled out. The guidelines specify that the concentration of $NO_2$ in the inspiratory flow must be guaranteed to be less than 2 ppm at all times. Strict monitoring requirements are laid out, including continuous monitoring of the oxygen concentration in the inspiratory gasflow; continuous percutaneous oximetry, arterial blood gas analyses including oxygen saturation; monitoring of central venous blood pressure; and determinations of blood methaemoglobin at least twice daily and for children under one year of age, at least four times daily.

In the prior art a blend of NO in $N_2$ is used with NO at concentrations of approximately 100 to 1000 ppm. Oxygen-free NO is mixed with air and thereby diluted to the desired final concentration immediately before administration to the patient. A flow controller should be used to achieve an appropriate blend of NO and air. All equipment should be regularly calibrated and a manual backup system should be available. To avoid risk to personnel working with NO inhalation therapy NO bottles should be kept in a well-ventilated room.

In all published reports of NO-inhalation therapy, an exogenous source has been used and the reports contain mentions of the safety precautions taken.

WO 92/10228 discloses an inhaler device for administering NO to a patient, said device comprising a vessel containing pressurized gas comprising at least 1 ppm NO; a housing defining a lumen, said vessel being attached to said housing to deliver said gas into said lumen; and a mechanism for controllably releasing said gas from said vessel into said lumen; said lumen being configured to route said released gas into the respiratory system of a person, and said device weighing less than approximately 5 kg. In the description only exogenous sources of NO are mentioned and the NO is said to be administered in concentrations ranging from 1 to 40 ppm and momentarily even increased to 80–180 ppm.

Further WO 91/14469 describes an apparatus and method for selective, separate or simultaneous collection and analysis of nasal and oral gases, respired by a patient, with optional simultaneous delivery to the patient of selected inhalant gases. The apparatus is specifically constructed and arranged to avoid or minimize contact with the patients's mouth or other facial surfaces. This is obviously far from the applications concerned in the present invention, that is collecting endogenous gases, in particular NO and supplying the same gases to an intubated or tracheostomized patient through the inhalatory flow of a ventilator. WO 91/14469 mentions the collection and analysis of various exhaled gases and, additionally the administration of oxygen or air, or a mixture of oxygen and air or of oxygen and water vapour and anaesthetic gases. No mention of administering an endogenous gas back to the patient can be found in the description or claims.

It is known that NO is endogenously produced in the upper airways of healthy subjects. NO is normally present in nasal air at concentrations ranging from 0, 1 to 5 ppm. The present inventors have found that the synthesis of NO in the upper airways is mostly carried out by a high producing "inducible like" NO synthase (NOS) situated in the epithelial cells of the paranasal sinuses. NO is probably also produced in the nasal cavity and in the nasopharynx. The present inventors have found that sinus derived air normally enters the nasal cavity through the ducts connecting the sinuses with the nose and is a large contributor to NO found in nasally exhaled air. In contrast, NO excretion in the lower airways and the lungs seems to be very low since tracheostomized patients exhibit only low NO levels when exhaling through the tracheostomy. Furthermore the high producing "inducible like" NOS described in normal paranasal sinuses is not normally present in the lower airways of healthy subjects. NO produced in the upper airways not only follows the airstream out with every exhalation but also flows down to the lower airways and lungs with every inhalation. Therefore a continuous low-dose NO flushing of the lower airways takes place normally in healthy subjects. However, patients with an endotracheal tube or tracheostomy are deprived of this self administration of NO since the upper airways, where most of airway NO production takes place, are by-passed by the intubation manoeuvre.

It is contemplated that also other endogenous agents, for example other gases or other endogenous, systemic or locally active agents, are synthesized in the upper airways. These agents can be any biologically active agent or agents, chosen from the group including hormones, enzymes, substrates, large molecular proteins, fractionated proteins, in the form of aerosols, droplets or gases. Patients with an endotracheal tube or tracheostomy are however deprived of the beneficial effects of these endogenous, biologically active agents. This can be especially significant in intubated or tracheostomized children, who normally breath almost exclusively through the nose.

SUMMARY OF THE INVENTION

The present invention as set forth in the appending patent claims eliminates the previously described safety problems associated with the administration of NO, including the possible occupational health risks to personnel administering NO therapy. The present invention restores the natural delivery of endogenous, biologically active agents, including NO to the lower airways occurring in healthy subjects. Additionally the apparatus according to the present invention, when integrated with or operated conjunctly with a ventilator, will reduce the negative side effects of artificial ventilation in intubated or tracheostomized patients. Therefore it is suitable for all intubated or tracheostomized patients during ventilator therapy. The apparatus according to the present invention additionally provides for safe and convenient administration of NO without interfering with the normal functions and safety requirements of a ventilator. The apparatus and method according to the present invention will additionally restore the administration of any hitherto unknown, endogenous, biologically active agent or agents to the lower airways.

The present invention eliminates the need for the first time the drawbacks of conventional treatment of intubated or tracheostomized patients. Not only are the risks, inherent with supplying exogenous NO, eliminated, the use of the new method, apparatus or system according to the present invention results in several beneficial effects. The present invention constitutes a break-through in that it reflects a radically new way of thinking, compared to the prevailing reasoning by persons skilled in the art, as represented by the publications and patent applications preceding the present invention.

BRIEF DESCRIPTION OF THE DRAWINGS

In the following are presented drawings for better understanding of the invention, whereby these drawings are in no way intended to limit the scope of the invention as set forth in the appended claims. In the drawings

DESCRIPTION OF THE PREFERRED EMBODIMENTS

In the following "upper airways" refers to the airways located above the vocal cords, including the paranasal sinuses, nasal cavity, nasopharynx, epipharynx, oropharynx, oral cavity and the hypopharynx. The term "nasal airways" refers to the airways extending from the nostrils to the nasopharynx. The term "endogenous NO" denotes nitric oxide produced within the body of a mammal, preferably a human. "Ventilator" denotes generally a machine that delivers air or an oxygen containing mixture of gases into the lungs of a patient who has insufficient breathing function, for example due to paralysis or sedation. The term "inspiratory airflow of a ventilator" is used to include the flow of gases through a ventilator, administered to a patient, extending from the source or sources of air and gas, e.g. containers of pressurized gases, to the lower end of a respiratory duct, cuffed or otherwise secured in the trachea of a patient.

According to the present invention air is collected from the upper airways in an intubated or tracheostomized mammal, preferably a human and said collected air is reintroduced to the inspiratory flow of a ventilator. Specifically said air contains endogenous, biologically active agents, such as NO from endogenous sources. Such endogenous. sources of NO are preferably the upper airways extending to the larynx. Another source of endogenous NO, related to the airways through the oesophagus, is the gastrointestinal tract. It is also contemplated that air, aspirated from the upper airways, could be collected from a patient prior to an operation requiring intubation and artificial ventilation of said patient, whereby this previously collected air, including endogenous NO could be administered to the patient. The possibility of donation, i.e. the administration of sterile filtered NO-containing air drawn from the upper airways of a donor to a patient with temporary or permanent lack of upper airway production of NO, should not be dismissed.

Naturally said air containing NO and possibly other biologically active endogenous agents, is collected in such a way that renders a NO-containing gas flow, suitable for introduction in the inspiratory airflow of a ventilator. If necessary the gas flow should be subjected to further treatment, such as filtering and similar treatment, well understood by one skilled in the art of gas therapy. Care should of course be taken not to denaturate or otherwise inactivate other beneficial, biologically active endogenous agents, possibly included in the gasflow.

Figure 1A:
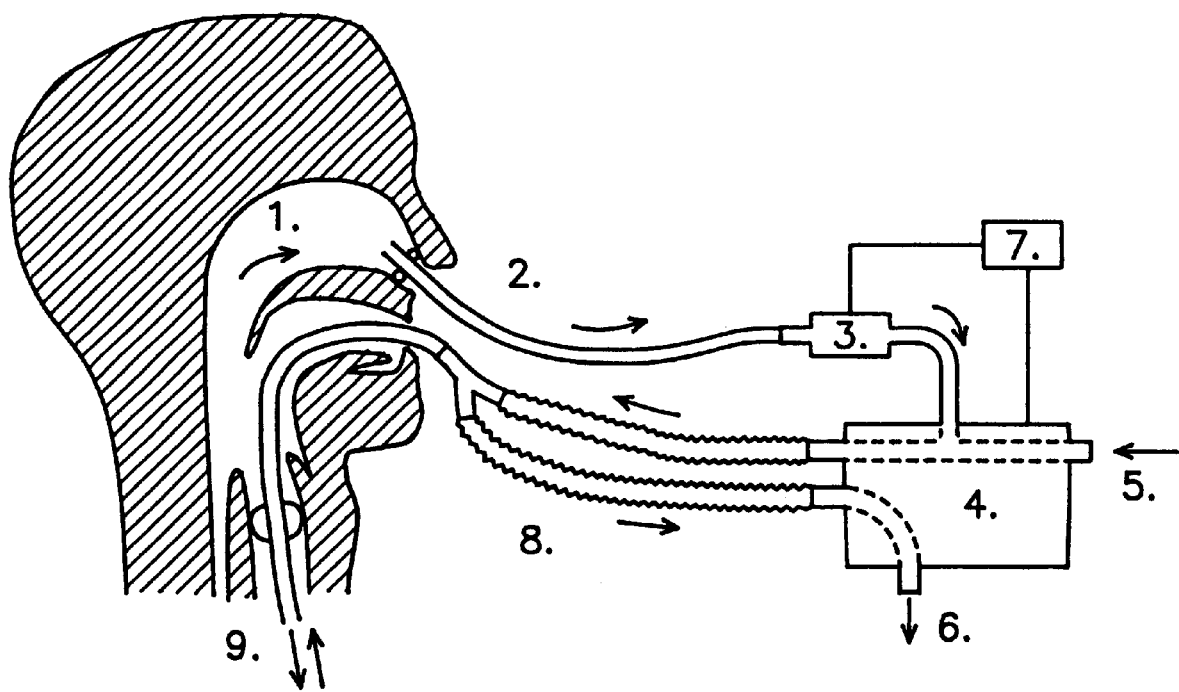
FIG. 1A is a schematic view of an apparatus according to the invention, including a transverse section of the upper airways.
Figure 1B:
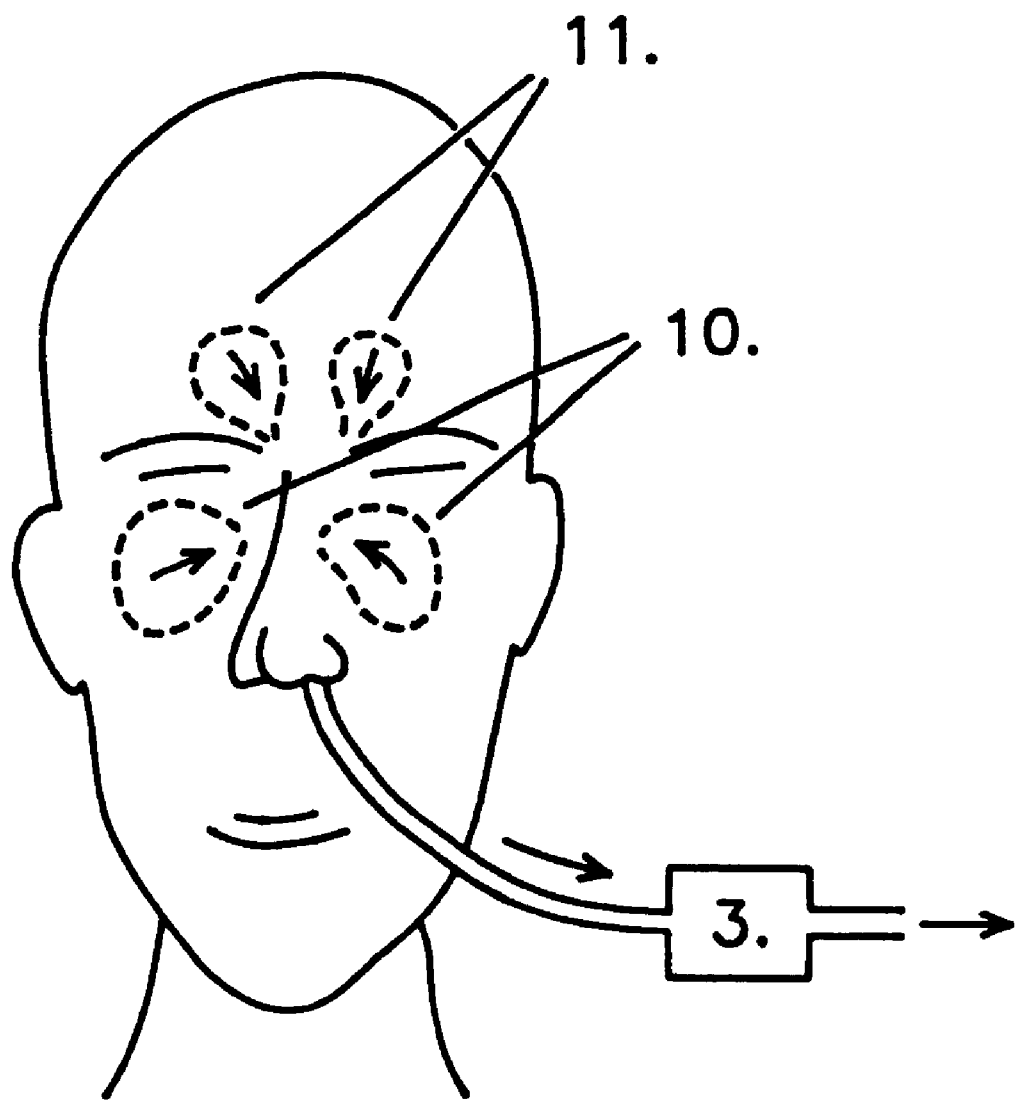
FIG. 1B is a schematic frontal view, showing the sinuses.

The invention will now be described with reference to FIG. 1A, where air is collected from the upper airways, preferably from the nasal cavity (1) by introduction of occlusive catheters into one or both nostrils (2, only one shown). The catheters are further connected via flexible tubing to a pump for aspiration of air. The pump unit (3) can further contain a filter and necessary valves, including a pressure release valve or valves to avoid any possible harm to the patient. The flow rate of the pump is controlled by a control unit (7) and can be adjusted within an interval of 0.001 to 5 l/min to optionally suit the given conditions (e.g. NO concentration, physionomy of the subject). The aspired air is led to a ventilator (4) having an inlet (5) for receiving air or a mixture of gases, including oxygen and an outlet (6) for venting the exhaled air. The ventilator is only schematically depicted and can naturally be any conventional ventilator. The ventilator is further connected, via respiratory tubes (8) to an endotracheal tube (9) cuffed in the trachea of a patient. Additionally a front view is shown in FIG. 1B, showing the location of the maxillary (10) and frontal sinuses (11) and the airflow in the same, when air is aspirated by a pump unit (3).

The aspiration of air is done either continuously or in a pulsating way, preferably in a pulsating way, i.e. that the pulse is set to aspirate air at preset intervals, simulating the natural breathing rhythm. The control unit (7) is preferably connected to the ventilator (4) for synchronization of the aspiration with the breathing movement. The option of blowing air, preferably moist air, back out through the nasal airways would be particularly preferable, as it further mimicks the natural airflow in unhindered breathing. It is highly probable, that the flow of air in and out through the nasal airways supports not only the normal functions of the sinuses but also improves the general conditions in the nasal airways.

Optionally both nostrils are connected to catheters, whereby ambient air is blown into one nostril while air is being aspirated from the other to further simulate natural breathing. Optionally both nostrils are aspirated and replenished simultaneously. In connection with a ventilator, functioning autonomously or in a patient triggered mode, the aspiration/blowing in the nostrils is synchronized with the functions of the ventilator.

Figure 2:
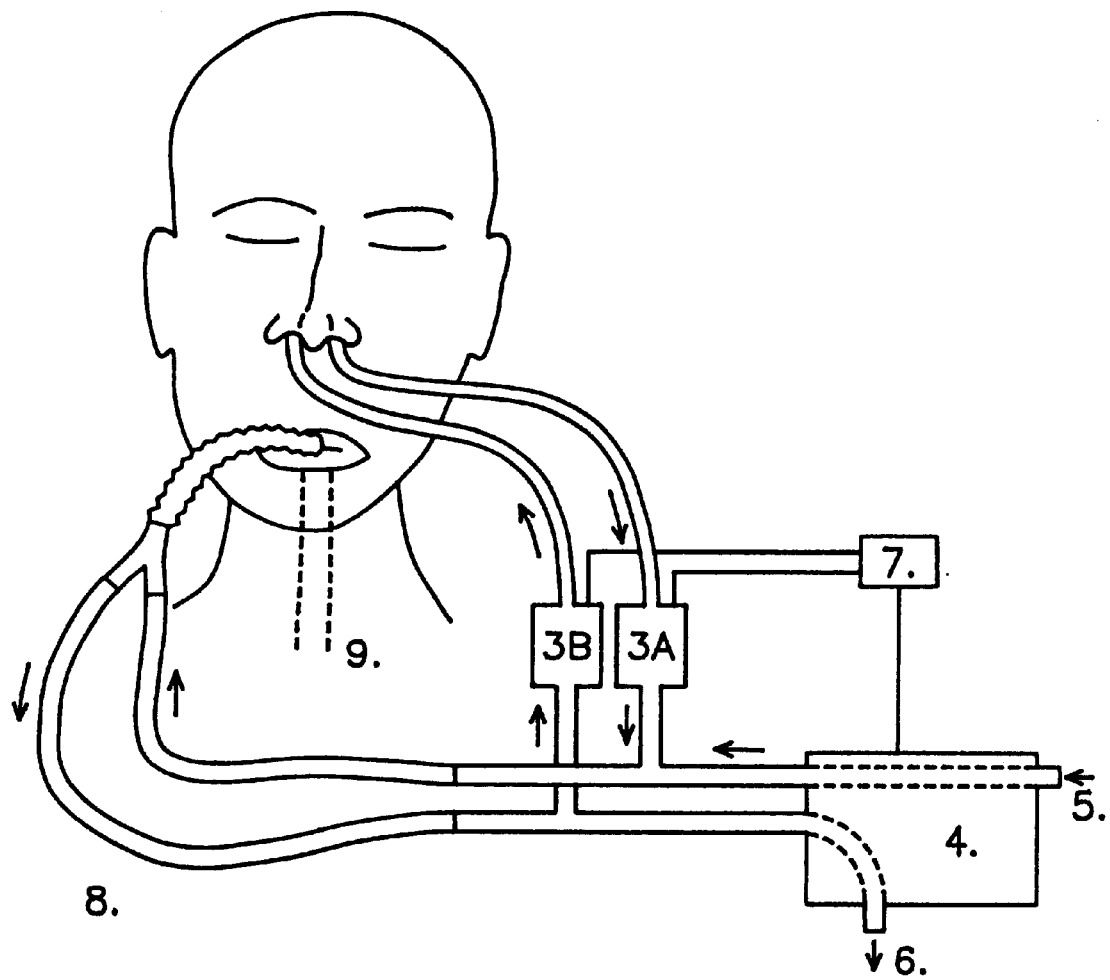
FIG. 2 is a schematic view of a preferred embodiment of the invention where moist air is reintroduced in the nostrils.

The aspiration of nasal air must be designed so as to achieve optimal amounts of beneficial, biologically active, endogenous agents, such as NO without causing damage to the nasal mucosa. Drying up of the nasal mucosa should be avoided. For this purpose a moisturizing filter can be applied to the catheter leading air into the nostrils. Optionally a part of the airflow exhaled by the patient can be returned to the nostrils, thereby utilizing the naturally occurring moisture in the exhaled air (See FIG. 2). In this setting a $CO_2$ absorbing filter (Not shown in the figure) is preferably used to avoid accumulation of $CO_2$ in the circulating air. In FIG. 2 catheters (2) are arranged in both nostrils and part of the moist exhaled air is taken from the exhalatory limb (8) and led back to the upper airways through one nostril while air is aspired from the other. Here the pump unit is replaced by two pump units (3A and 3B) both controlled by control unit 7, connected to the ventilator. The ventilator further has an intake (5) for receiving exogenous gases or air and an outlet (6) for venting exhaled air. The respiratory limb of the ventilator is connected to an endotracheal tube (9, shown as dashed lines) cuffed in the trachea of the patient. Using a simple three-way valve or similar connection (not shown) the aspiration/pumping can be alternated between the nostrils. The degree of desiccation can also be influenced by keeping the aspiratory flow rate as low as possible.

An embodiment of the invention, not shown in the appended drawings, aims at further mimicking the natural breathing pattern of a mammal, i.e. nasal breathing. In this, embodiment air is aspirated from the nasopharynx through a catheter or catheters, introduced orally, running parallel to the endotracheal tube. Thereby air is aspirated inwards, through the nose, in a manner more similar to normal breathing. This embodiment further makes possible the blowing of air, preferably moist air, outwards through the nasal airways. This further mimicks the natural breathing pattern and associated airflows, aiding the normal functioning of the sinuses and the general balance in the nasal airways. A hypothesis, based on the geometry of the nasal airways and the sinuses, would be that gas is aspired from the sinuses in the inhalation phase and, consequently, that the sinuses are replenished with air in the exhalation phase.

The NO concentration delivered to the inspiratory airflow of a ventilator should be such that the concentration in the air delivered to the patient is in the interval of 5 to 200 ppb (parts per billion) during continuous delivery. Alternatively the collected NO can be temporarily stored in a vessel, made of NO non-absorbing material, e.g. glass, steel or an appropriate plastic, conventionally used in the field of medicine, e.g. Teflon®. Preferably said vessel is a flexible, bellows-like vessel made of Teflon® or equivalent material. Using such a reservoir higher doses of NO can be released in the inspiratory airflow of an ventilator at preset intervals. The mean concentration of NO delivered to the patient should preferably still be less than 1 ppm (part per million).

The aspirated air containing NO and possible other biologically active agents is introduced in the inspiratory airflow of a ventilator either continuously or collected in an intermediate reservoir and released intermittently, for example introduced with intervals of a preset number of breaths.

Although the present invention primarily concerns collecting air from the upper airways, including biologically active agents, such as endogenous NO and supplying it to the inspiratory airflow of a ventilator connected to an intubated or tracheostomized patient, it can naturally also be practised in connection with a ventilator connected to a laryngeal mask, applied on the patient. When a facial mask is used, in connection with a ventilator or a source of air or oxygen, the supply of endogenous NO is contemplated only when the patient has insufficient NO synthesis in the upper airways or is unable to breath through the nose. The extraction of endogenous NO from the upper airways is contemplated also for patients being chronically tracheostomized and thus deprived of their natural NO.

Generally the administration of endogenous NO is contemplated for supply to the inspiratory airflow of a ventilator or similar device for restoring pulmonary function and improving non-specific host defence in the airways of all intubated or tracheostomized patients. The present invention aims to supplement air from the upper airways to the lower airways, i.e. restore the circulation of air taking place during normal breathing. Therefore it is thought to be of use as a standard procedure in all intubated or tracheostomized patients irrespective of diagnosis.

The biological effects of NO extend beyond vasodilatation. Thus, NO has also bacteriostatic and antiviral properties and has been shown to increase ciliary beat frequency in respiratory epithelium. All these properties of NO may be of importance in normal unspecific host-defence of the airways. Therefore, inhibition of normal airway NO synthesis may increase susceptibility to respiratory tract infections. That is what happens in intubated or tracheostomized subjects since the main supply of endogenous NO to the lower airways is disconnected. Indeed, it is known that long-term ventilated patients have impaired mucociliary clearance and that they are almost obligatory colonized by bacteria in the trachea and the lower airways, often resulting in severe lower respiratory tract infections. Furthermore, children with Kartagener's syndrome (a triad consisting of sinusitis, bronchiectasis and sinus inversus) lack NO excretion in the upper airways and these patients have severe problems with repeated airway infections including bronchitis and pneumonia. Children in general are an important patient group as the inventive method would help to avoid the previously described risks of administering exogenous NO and simultaneously restore the natural nasal breathing pattern typical for children.

The present invention restores the normal low-dose flushing of the lower airways with air from the upper airways, containing NO and possible other biologically active agents. This leads to a reduction in pulmonary vascular resistance and improved oxygenation. Furthermore, endogenous NO may prevent airway infections caused by bacteria, virus, fungi or other pathogens and may also improve mucociliary clearance.

Sinusitis is a common problem among long-term ventilated patients. Up to 70% of these patients show non-pneumatized sinuses on X-ray. A common cause of sinusitis in general is thought to be a swelling of the mucosa surrounding the ostia, leading to impaired ventilation and drainage of the sinuses. The present invention may help to avoid said poor ventilation of the sinuses by airflow applied to the nasal airways. This airflow may prevent swelling of the sinuses and improve ventilation of the sinuses by simulating the normal breathing cycle. Indeed, earlier studies have shown that the ventilation of the sinuses is improved by nasal breathing.

It is contemplated that the administration of endogenous NO increases the uptake of pulmonary administered pharmaceuticals and simultaneously, that certain pharmaceuticals potentiate the effect of the endogenous NO. Consequently it is suggested by the present inventors that pharmaceutical agents are introduced in the flow of gases containing endogenous NO derived from the upper airways before introduction in the inspiratory airflow of a ventilator or similar device. Thus the apparatus for feeding nasal air, including endogenous NO to the inspiratory airflow of a ventilator can be used as a convenient route for administration of pharmaceutical agents in the form of aerosols or fine powders, without interfering with the normal functions of the ventilator.

EXAMPLES

The present inventors investigated whether the restoring of the normal flushing of the lower airways with gases collected from the upper airways, including the normal low-dose NO inhalation, would influence pulmonary vascular resistance (PVR) and arterial blood oxygenation in intubated patients.

Figure 3:
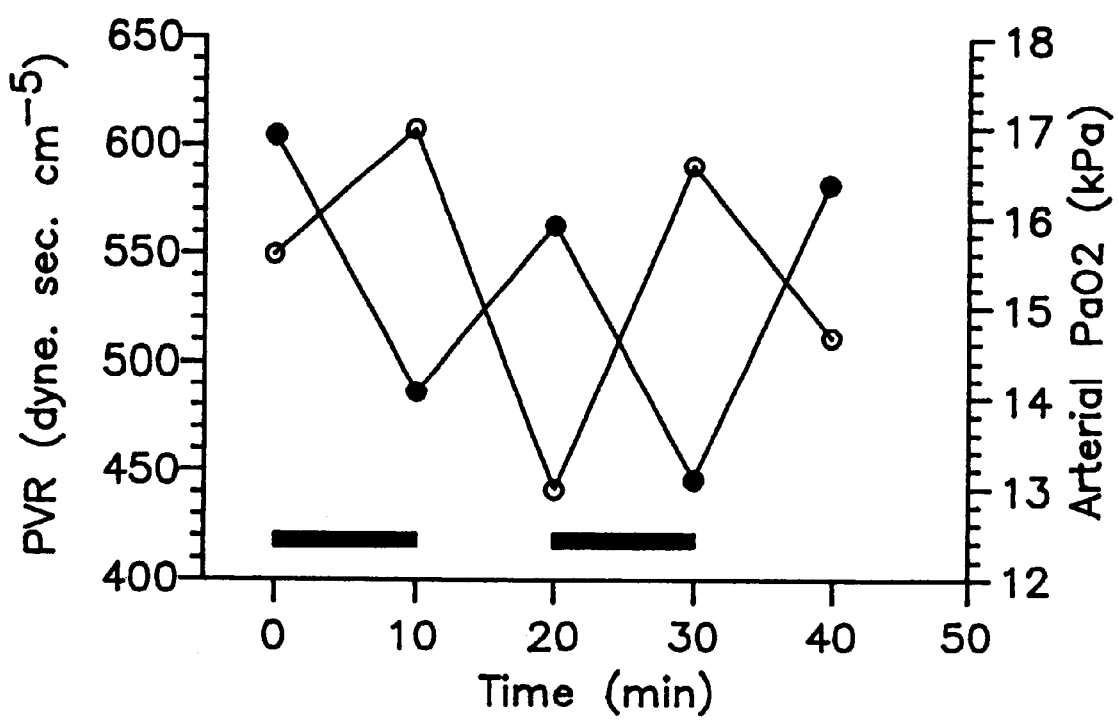
FIG. 3 is a graph, showing the effects of intermittently applied sub ppm doses of NO on pulmonary vasculatory resistance and oxygen saturation in blood of ventilated patients.

In the experiments gases were collected from the upper airways of the patients by aspiration (2 l/min) from one nostril and led into the inhalation limb (i.e. the inspiratory airflow) of a standard ventilator. 15 patient were studied. The NO concentration in inhaled air, after addition of the nasally derived air was in the interval of 5 to 45 ppb with the aspiration method used. In comparison less than 2 ppb NO was inhaled by the patients when no nasally derived air was introduced. The results are presented in FIG. 3. The graphs show the effects of self-administration of nasal gases on pulmonary vascular resistance (PVR, filled circles) and arterial oxygenation ($PaO_2$, empty circles) in an intubated subject. Air was aspirated in repeated 10 min periods, either from a nostril of a patient (bars) or from ambient air (NO<3 ppb) and reintroduced into the inhalation limb of a ventilator. Measurements of PVR and $PaO_2$ were made at the end of the 10 min periods.

In 70% of the patients, an acute rise in arterial $PaO_2$ in the range of 8 to 25%, was observed when adding nasal air to the inspired air. Furthermore, in five patients the pulmonary vascular resistance decreased by 15±4% during the same procedure. Similar responses were observed when exogenous NO at the same concentration was added to the inspired air. The results indicate that endogenous NO and possibly other biologically active agents, produced in the upper airways, are involved in the basal regulation of PVR through continuous low-dose self inhalation. Mechanically ventilated patients are deprived from self inhalation of endogenous NO and other possible endogenous substances and replacement of this loss may improve vital pulmonary functions.

An apparatus according to the present invention can preferably be included as a standard feature in ventilators. Likewise the method according to the present invention can be included as a standard procedure in the treatment not only of mechanically ventilated patients but also of any person with restricted inhalatory flow through the upper airways.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

What is claimed is:

1. A method for treating a patient having been intubated or tracheostomized, by inserting an endotracheal tube into the patient's trachea, thereby physically separating the upper airways from the lower airways of the patient, wherein said upper airways comprise all airways above the patient's vocal cords, and said lower airways comprise all airways below the patient's vocal cords, comprising the steps of:

connecting said endotracheal tube to a ventilator; and transferring gases from the upper airways to the lower airways;

wherein said gases include endogenous nitric oxide (NO).

2. A method for treating a patient having been intubated or tracheostomized, thereby physically separating the upper airways form the lower airways of the patient, wherein said upper airways comprise all airways above the patient's vocal cords, and said lower airways comprise all airways below the patient's vocal cords; comprising the steps of:

inserting an endotracheal tube into the patient's trachea;

connecting said endotracheal tube to a ventilator;

connecting the upper airways of the patient to an aspirating device and;

transferring gases from the patient's upper airways to the patient's lower airways;

wherein said gases include endogenous nitric oxide (NO).

3. The method of claim 2 further comprising:

leading the gases to the inspiratory airflow of a ventilator.

4. The method of claim 3 further comprising:

operating said aspirating device continuously.

5. The method of claim 3 further comprising:

operating said aspirating device intermittently.

6. The method of claim 3 further comprising:

releasing the gases periodically to the inspiratory airflow of the ventilator.

7. The method of claim 2 further comprising:

introducing moist air in the nostrils of the patient to prevent desiccation of the nasal mucosa.

8. The method of claim 3 further comprising:

synchronizing the aspirating device with the breathing rhythm of the patient.

9. The method of claim 3 further comprising:

blowing air out through the nasal airways of the patient in a manner mimicking normal exhalation.

* * * * *